United States Patent [19]

Campbell

[11] Patent Number: 4,863,610

[45] Date of Patent: Sep. 5, 1989

[54] SCRAPING, COLLECTING & ELUTING APPARATUS FOR THIN LAYER CHROMATOGRAPHY AND METHOD FOR ITS USE

[76] Inventor: Brian D. Campbell, P.O. Box 2926, Kensington, Md. 20895

[21] Appl. No.: 60,402

[22] Filed: Jun. 11, 1987

[51] Int. Cl.$^4$ ...................... B01D 11/02; B01D 15/08
[52] U.S. Cl. ................................. 210/658; 73/61.1 C; 210/772; 210/198.3; 422/61; 422/70; 422/101; 436/178
[58] Field of Search ........... 73/61.1 C, 863.23, 863.24, 73/863.25; 210/198.2, 198.3, 658, 772; 422/61, 70, 101; 436/178

[56] References Cited

U.S. PATENT DOCUMENTS

| | | | |
|---|---|---|---|
| 3,215,500 | 11/1965 | Bittner | 422/101 |
| 3,465,884 | 9/1969 | Matherne, Jr. | 210/658 X |
| 3,513,092 | 5/1970 | Matherne, Jr. | 210/658 |
| 3,676,073 | 7/1972 | Luckey | 436/178 |
| 4,214,993 | 7/1980 | Forsythe, Jr. et al. | 210/198.2 X |
| 4,261,835 | 4/1981 | Creeger | 210/198.3 X |
| 4,422,941 | 12/1983 | Vaughan, Jr. et al. | 210/657 |
| 4,438,205 | 3/1984 | Saint-Leger et al. | 436/178 X |

FOREIGN PATENT DOCUMENTS 796010 6/1958 United Kingdom ............. 73/863.23

OTHER PUBLICATIONS

Hay et al., "Some Useful Techniques in Thin Layer Chromatography", Laboratory Practice, vol. 23, No. 9 (Sep. 1974), pp. 483 & 484.
Allied Fisher Scientific catalog, 1986, p. 287.
Alltech Associates catalog, 1986, p. 302.
American Scientific Products, "Chromatography Products" catalog, 1984, pp. 346 and 347.
American Scientific Products General Catalog, 1987-88, p. 542.
Anspec, "Chromatography: Liquid and Thin Layer" catalog, 1984, pp. 276 & 285.
Thomas Scientific catalog, 1986-87, p. 288.
VMR Scientific catalog, 1987-88, p. 440.
Whatman, Inc., "Thin Layer Chromatography Products" catalog, 1983, pp. 17 & 23.

Primary Examiner—Robert Spitzer

[57] ABSTRACT

A device and method for scraping and collecting adsorbent from located areas on developed thin layer chromatography plates and extracting substances from collected adsorbent. The above functions can be performed without additional apparatus. The device is constructed of polypropylene to allow for easy use, manufacture and low cost. The shell surrounds a primary filtering and retaining material and a secondary filter. The adsorbent is removed from the thin layer chromatography plate via a scraping edge and collected by aspirating the adsorbent into the device where it becomes embedded in the primary filtering and retaining material. The device can then be separated to allow facile addition of a solvent to elute the sample out of the device free of adsorbent. The scraping process is improved as a result of the polypropylene contact with the plate, the collection process minimizes loss of removed adsorbent, and the elution/filtration allows easy recovery of developed samples. These functions are accomplished within this device and therefore time spent in preparation and cleanup is kept to a minimum. This device is potentially disposable.

20 Claims, 4 Drawing Sheets

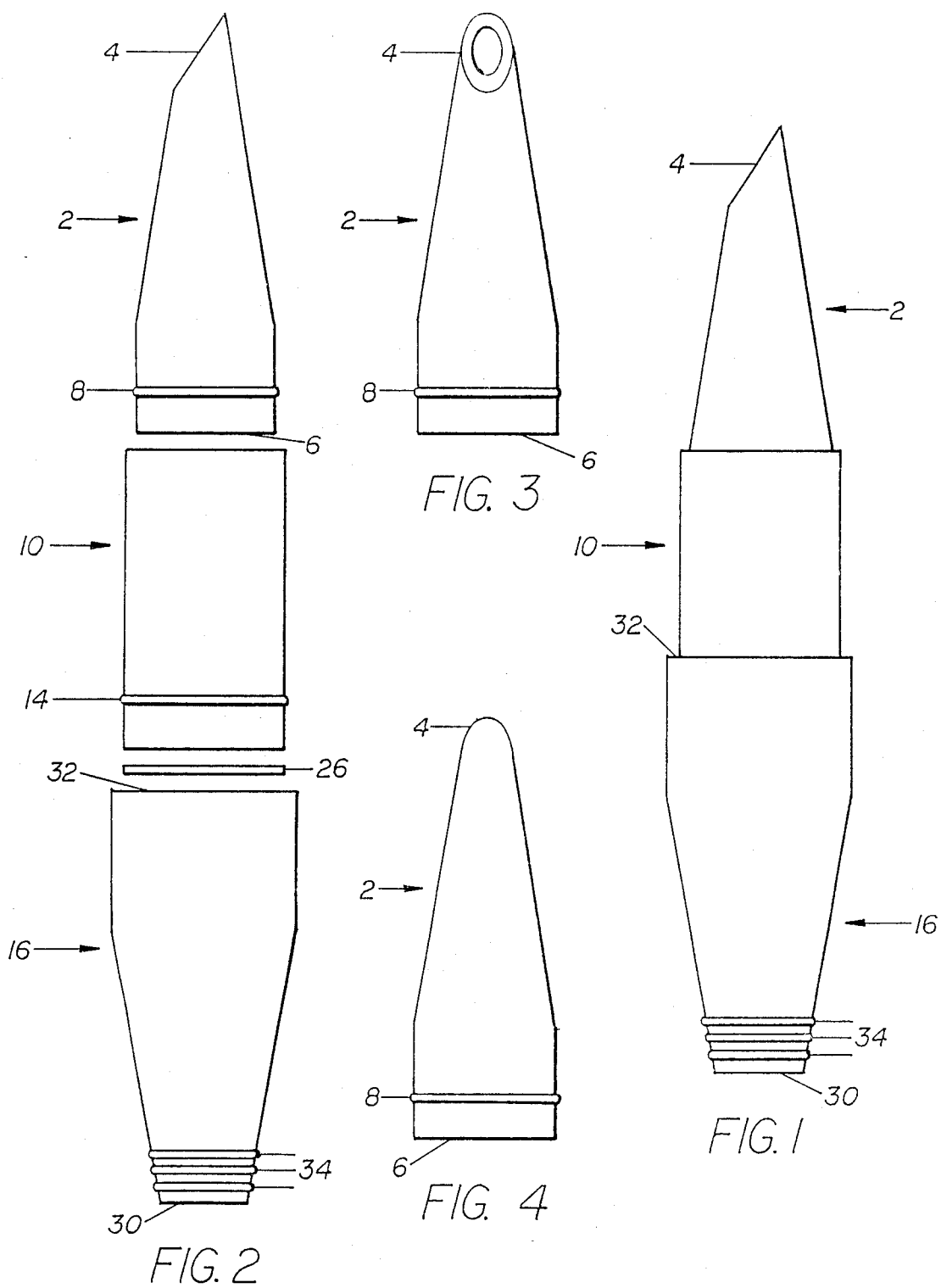

SCRAPING, COLLECTING & ELUTING APPARATUS FOR THIN LAYER CHROMATOGRAPHY AND METHOD FOR ITS USE

BACKGROUND—FIELD OF THE INVENTION

This invention relates to a device and method used in medical, chemical and biological laboratories, primarily with thin layer chromatography.

BACKGROUND—DISCUSSION OF THE PRIOR ART

Heretofore, it has been a repetitive and tiresome chore to accurately recover the adsorbent from located areas of developed thin layer chromatography plates, and then/to extract the desired substances from the adsorbent.

Small rigid metal spatulas, razor blades, and specially designed metal scraping tools are employed to remove the adsorbent from the plate, and to transfer it to a receptacle. This presents unnecessary delays and uncertainty to the scientist: (1) the metal spatula is too stiff to easily scrape the plate completely clean as it is not flexible to easily conform to the the plate during contact, hence it is time consuming and difficult to remove all of the adsorbent. (2) transfer of the detached adsorbent to a receptacle is accomplished with the potential for loss of adsorbent, a portion may be spilt unnoticed, some may remain on the spatula or on the materials used to transfer the adsorbent.

After the transfer of adsorbent to a receptacle, a means for removing the substance from the adsorbent is often necessary, elution and filtration being the most obvious and facile. Different methodologies can be used for this process: suspend the adsorbent in a suitable solvent and then pour the suspension through a filtration device, or place the adsorbent in a filtration device and pour a suitable solvent over the adsorbent. The solvent elutes the substance from the adsorbent and the eluate passes through the secondary filter. The resulting solution can be evaporated, leaving the purified substance. These methods are time consuming in preparation and clean up, particularly if the number of samples is large (each sample has to be treated independently to avoid contamination by the others), and if specific cleanup precautions are warranted while using radioactive isotopes.

Developments have led to use of vacuum assisted recovery apparatus to remove the adsorbent from the thin layer chromatography plates:

Glass pasteur pipettes were plugged with cotton or glass wool to allow air flow but not adsorbent flow through the pipette. The tapered end of the pipette was used to scrape the adsorbent from the thin layer chromatography plate while the other end of the pipette was attached to a vacuum tubing. The scraped adsorbent was aspirated into the pipette and embedded in the glass wool or cotton. The loss of adsorbent during scraping and collection was lessened. This decreased the drudgery of the scraping process although the lack of flexibility in the metal contact with the plate mentioned earlier is of equal if not greater detriment in the glass to plate contact. Additionally, the tip of the pipette would easily break if too much pressure was applied to the thin layer chromatography plate with the pipette, and the small diameter of the tip opening made scraping slow and tedious because the volume of adsorbent removed with each pass was very small.

Recovery of the substance in the adsorbent was only slightly improved. The glass wool or cotton needed to be removed from the pipette, still presenting the potential loss of adsorbent during transfer. If filtration was required, it still needed to be performed in similar fashion to that described above. Additionally, special precautions must be taken in disposal of glass especially if radioactive isotopes are used.

Improvements have led to the Chromovacs TM "Spot Recovery Device" manufactured by Spectrum Medical Industries, Inc, "Sample Recovery Tubes" manufactured by Whatman, Inc. and Wheaton Industries, "Recovery Tubes" manufactured by Alltech Associates, and the "TLC Zone Recovery Pipet" manufactured by Radnoti. These have alleviated some of the problems of inaccuracy, inconsistency, and costly time consumption, but not all. Being constructed of nonflexing glass, they are unable to easily scrape the thin layer chromatography, are breakable in shipping and usage (which can frustrate both retailer and customer), non-repairable, and potentially injurious. All these products are vacuum assisted and aspirate the adsorbent into a chamber where it is embedded in a glass wool plug or some type of filter.

Chromovacs TM "Spot Recovery Device" is simply a cylinder tapered at both ends with a glass wool plug in the middle. It is not much of an improvement over the stuffed pasteur pipette in function as the glass wool still needs to be removed from the tube and manipulated as described above, still presenting the problem with transfer and filtering. It is not reusable and has a function limited to scraping and collecting the located area. Disposal problems are the same as with pasteur pipettes. Their cost ranges from $31.50 to $34.00 per package of 25.

Whatman, Inc.'s "Sample Recovery Tubes" have some advantages in function, but lose those advantages in cost, each tube ranging from $25.00 to $40.00. It is similar to Spectrum Medical Industries, Inc.'s Chromovacs TM with an added improvement: instead of a glass wool plug it has a permanent glass microfiber filter. They can be purchased in different sizes to accomodate different volumes of scraped adsorbent (0.5, 1.5, and 30 ml) and with a "medium" (in the 0.5 or 1.5 size) or "coarse" (in the 30 ml size) filter porosity. In addition to scraping and collection, it also can be used to filter out the adsorbent, allowing the substance to be extracted without the use of other apparatus. However, it is awkward to apply the solvent through the opening of the tube due to its small size. Furthermore, the permanent filter is of no advantage if a filtration process using a different porosity from the installed glass microfiber filter is required. One is not able to vary the filter and therefore is not able to vary the porosity of the filtration. It is marketed as reusable, but difficult to clean, also due to its small openings and the fact that it does not separate. It is expensive and unless one can afford to purchase many, the handling of numerous samples simultaneously can become even more tiresome as the tube would need to be cleaned repeatedly between samples.

The "Sample Recovery Tube" manufactured by Wheaton Industries is more complex. The collection chamber can be adjusted to accomodate different volumes of adsorbent removed. The adsorbent is aspirated into the device and trapped on a permanent frit or disposable filter paper. The method of scraping, collecting and eluting the sample is similar to the method outlined for Whatman's product with the exception that the disposable filter paper can be removed before elution. The device separates into many parts and comes with a 5 ml funnel to facilitate the elution process. There are many small pieces to this device which can be easily broken or lost. It is also time consuming to clean, and expensive to replace as they cost $51.05. Their high price also makes it very costly to purchase many for simultaneous use.

The "Recovery Tube" marketed by Alltech Asssociates is virtually the same as the "Sample Recovery Tube" manufactured by Whatman, Inc. It is available in varying chamber volumes of 1, 2 and 25 ml. These are more costly than Whatman's, ranging from $45.00 to $54.00. Similarly, they are difficult to use and clean, and they offer no filtration variation.

Radnoti's "TLC Zone Recovery Pipet" is only useful for recovering small volumes of adsorbent. The adsorbent is aspirated onto a filter disc where it is trapped. After disassembling the pipet, the disc is removed and either centrifuged to dislodge the scraped adsorbent or eluted to recover the substance in the adsorbent. It, like Wheaton's "Sample Recovery Tube", separates into many parts and gaskets which can easily be lost. It too is very expensive: $54.00 each; replacement filter discs costing $21.60 for 6 ($3.60 each), and replacement gaskets costing $8.40.

Other devices employing similar methods of aspirating the adsorbent from the plate capture the adsorbent in small test tubes or embed the adsorbent in thimbles of porous plastic or other similar material. These also are expensive: a "Zone Collector" manufactured by DESAGA GmbH in Heidelberg, West Germany sells for $29.00 to $30.00 each, and the thimbles are $55.00 per lot of 25 ($2.20 each). Some of these devices require scraping with a spatula prior to their use. These methods, while making improvements, are expensive, cumbersome and still require the lengthy handling of samples to extract the desired substance from the adsorbent enmeshed in the thimble or caught in the test tube.

SUMMARY OF THE INVENTION

What is required is a facile, quick, accurate, and consistent method to remove the adsorbent from the located area on the developed thin layer chromatography plates, collect the scraped adsorbent, and extract the substance from the collected adsorbent. Ideally this would be done at a low enough cost to more than compensate for the money expended to purchase the apparatus in both time saved as well as in the increase of experimental reliability.

According several objects and advantages of the present invention meet these requirements:

The present invention is versatile: it is a scraper, collector and extractor. It completes all three functions easily in one small apparatus, eliminating the loss of adsorbent in both collection and transfer because scraping, collection, and extraction are accomplished within the same device. The device contains a filtration means that can be varied for different applications; filters of differing porosities and solvent resistances can be interchanged. It can accomodate an unlimited range of adsorbent volumes, depending upon its construction.

The present invention gives precise, reliable, consistent results and is easier and quicker to operate than other methods available. It is lightweight, compact and is made to fit comfortably in one's hand. This apparatus is easily disassembled, and reassembled, and its parts can be cleaned and replaced if a reusable market is taken. It has a broad scraping edge giving a large area of contact between the edge and the plate, allowing removal of a large volume of the adsorbent with each pass of the device over the thin layer chromatography plate. The device saves time, and the time saved increases exponentially as more samples are handled.

It can be molded of durable, inexpensive, disposable, solvent resistent, rigid but flexible polymers such as polypropylene, allowing conforming contact between the scraper and the thin layer chormatography plate. The present invention does not need to be made of glass, eliminating the possibility of breakage, injury and resulting liability. It can be manufactured, assembled and packaged easily at low cost, less than $0.12 each in large quantities, allowing a much lower cost alternative to scientists, and a large margin for profit for manufacturers. This apparatus can be marketed as disposable or reusable, either way allowing greater savings in time and money than other similar existing products, potentially capturing the market.

These objects and advantages of the invention alleviate the disadvantages of the aforementioned products. Other methods present difficulties in removing the adsorbent, collecting all of the adsorbent without loss, transfering the adsorbent without loss, and eluting the desired substance from the adsorbent without lengthy preparation, cleanup and usage of additional laboratory equipment. They are also very costly. Further advantages and objects of my invention will become apparent from a consideration of the drawings and ensuing description of it.

This invention has a surface for scraping the adsorbent off the thin layer chromatography plate and a reservoir to accomodate the adsorbent after it has been scraped from the plate. A vacuum source is connected to this device to aspirate the adsorbent into the reservoir after it has been removed from the plate. A removeable, exchangeable and therefore variable filtration means is used to retain the collected adsorbent in the invention. This device can be separated into its different parts to further facilitate it's use.

On one piece is a surface for scraping and manipulating the adsorbent. This portion attaches to another piece which accomodates the collected media. This second piece connects to a third piece which connects the whole device to a vacuum source. A gas and liquid permeable filter is located at the junction of the second and third pieces. All of these connections are airtight and use snap together fittings that are separable by hand strength and dexterity.

The reservoir is bordered on one side by the filter and on the other side by a retaining screen. This reservoir contains a filtering and retaining material such as glass wool or cotton that allows the adsorbent to easily embed itself in it, does not allow the adsorbent to easily escape. The retaining screen keeps the primary filtration material from inadvertantly being removed from the device. The filter serves to retain the adsorbent in the device during elution while allowing the solvent and desired soluble sustance (organic and inorganic compounds) to pass therethrough.

Although inexpensive, disposable polypropylene is recommended, the material from which the device is constructed may be one that will allow cleaning, autoclaving and reuse.

This device allows the functions of removal of adsorbent from the thin layer chromatography plate, collection of the removed adsorbent, and extraction of substances embedded in the adsorbent to be acomplished without additional laboratory apparatus.

This device can also be made into kit through the interchangeability of parts and the addition of a funnel. The funnel addition will allow a greater volume of liquid to flow through the device and facilitate the extraction process. This funnel is addable to the device using an attachment similar to the scraping portion mentioned earlier.

This method quickly, easily and accurately recovers located samples on developed thin layer chromatography plates with a single device by (1) detaching the adsorbent from the plate with the scraping portion, (2) aspirating the detached adsorbent into the device via attachment to a vacuum source, (3) collecting the adsorbent in a chamber located inside the device, (4) separating the device into a plurality of parts, (5) eluting the substances from the captured adsorbent, (6) filtering the resultant eluate. The resultant solution may then be collected and subjected to evaporation to recover the sample in a pure and dry form. This method can be enhanced by the addition of the funnel to allow easier addition of a solvent and therefore facilitate the elution process.

BRIEF DESCRIPTION OF THE DRAWINGS

FIG. 1 is a side view showing the device assembled and ready for use;

FIG. 2 is a side view of the device disassembled showing its different parts separately;

FIG. 3 is a bottom view showing the scraping portion of the device;

FIG. 4 is a top view showing the scraping portion of the device;

Figure 6:
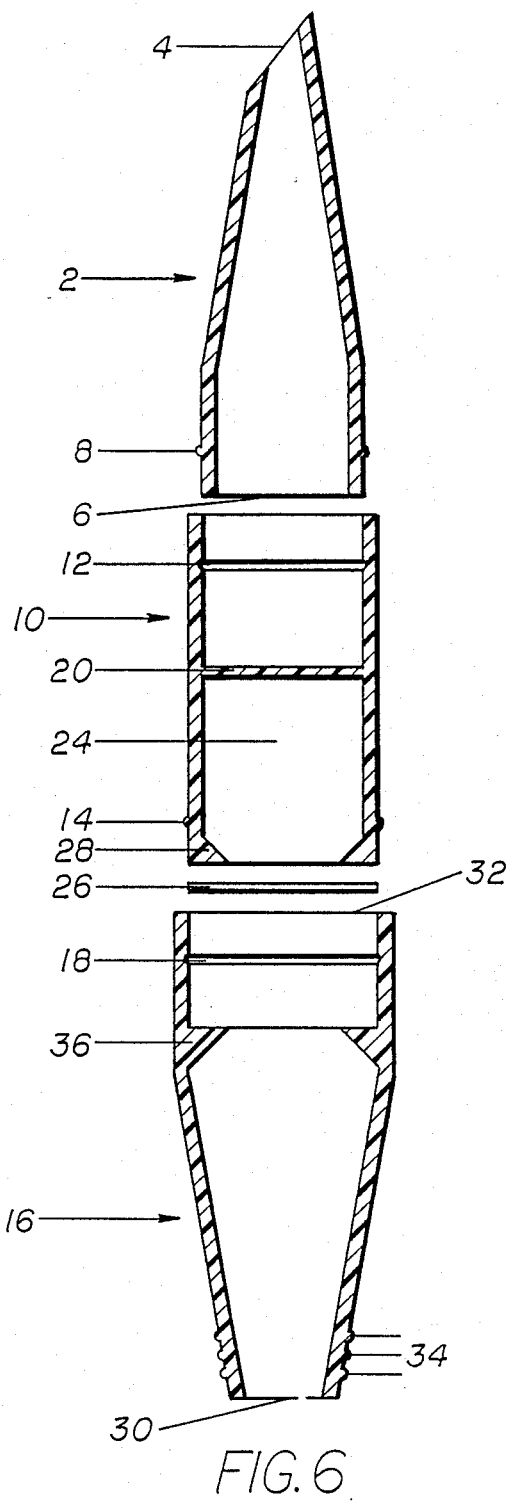
FIG. 6 is a cross-sectional side view showing the device of FIG. 2 disassembled to reveal its separate parts without the primary filtering material.

LIST OF REFERENCE NUMERALS:

2—scraper
4—tip of scraper, scraping edge
6—base of scraper
8—raised bead on scraper
10—collector
12—recess in collector
14—raised bead on collector
16—vacuum attachment
18—recess on vacuum attachment
20—retaining screen
22—primary filtering and retaining material
24—reservoir
26—gas and liquid permeable filter
28—filter securing lip
30—tip of vacuum attachment, apex of vacuum attachment
32—base of vacuum attachment
34—series of raised beads on vacuum attachment
36—filter holding lip
38—funnel
40—base of funnel
42—top of funnel
44—neck of funnel
46—raised bead on funnel

DETAILED DESCRIPTION OF THE INVENTION

Figure 7:
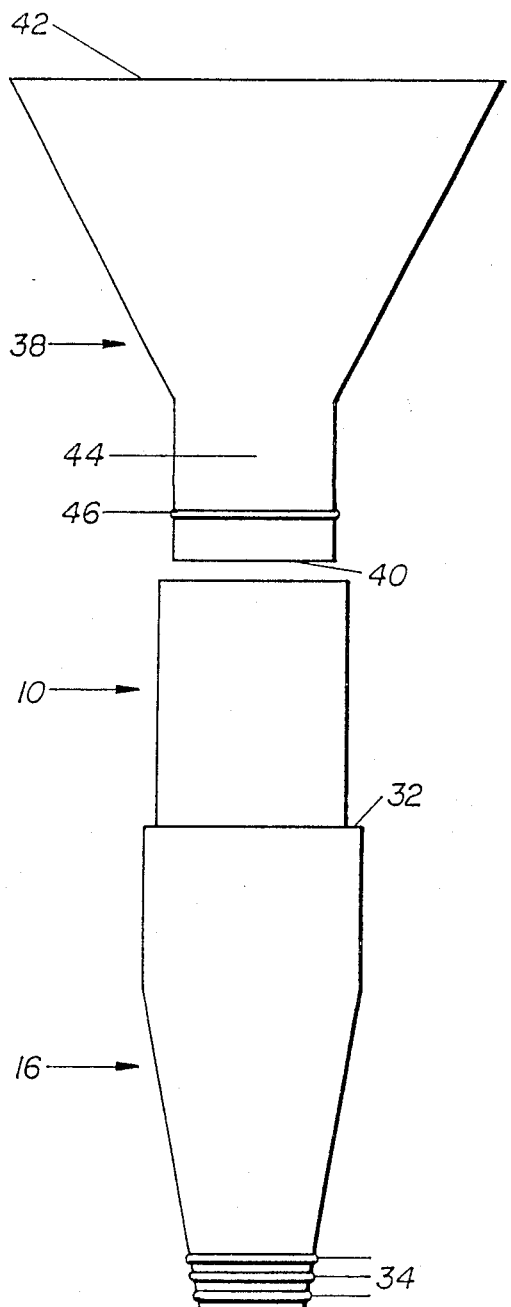
FIG. 7 is a side view showing the device with the scraping portion of the device removed and the funnel in position to be fastened to the device.
Figure 8:
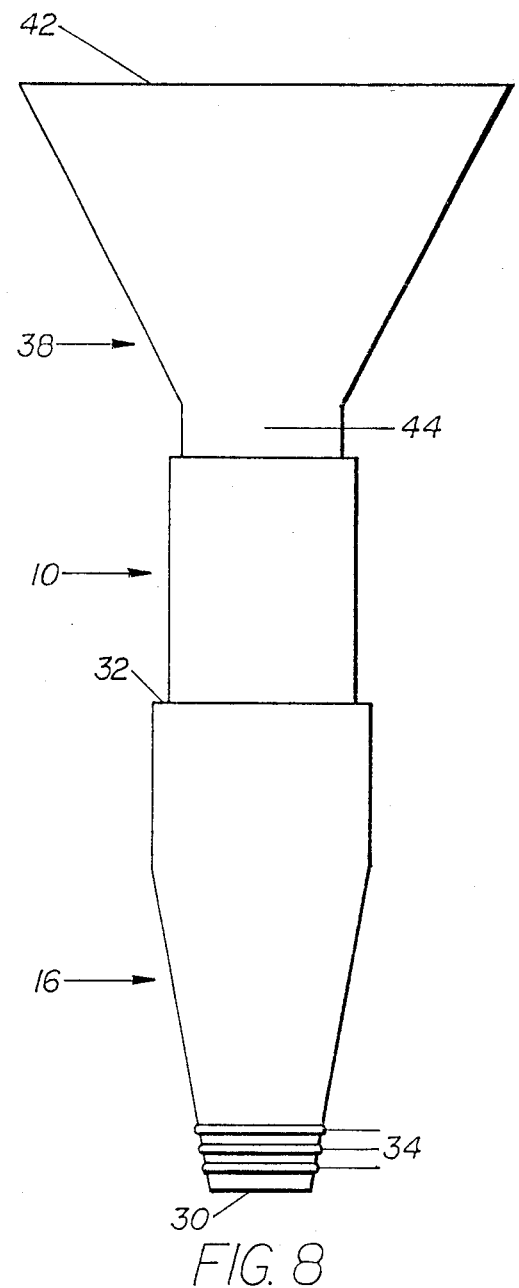
FIG. 8 is a side view showing the device with the scraping portion removed and the funnel attached.
Figure 9:
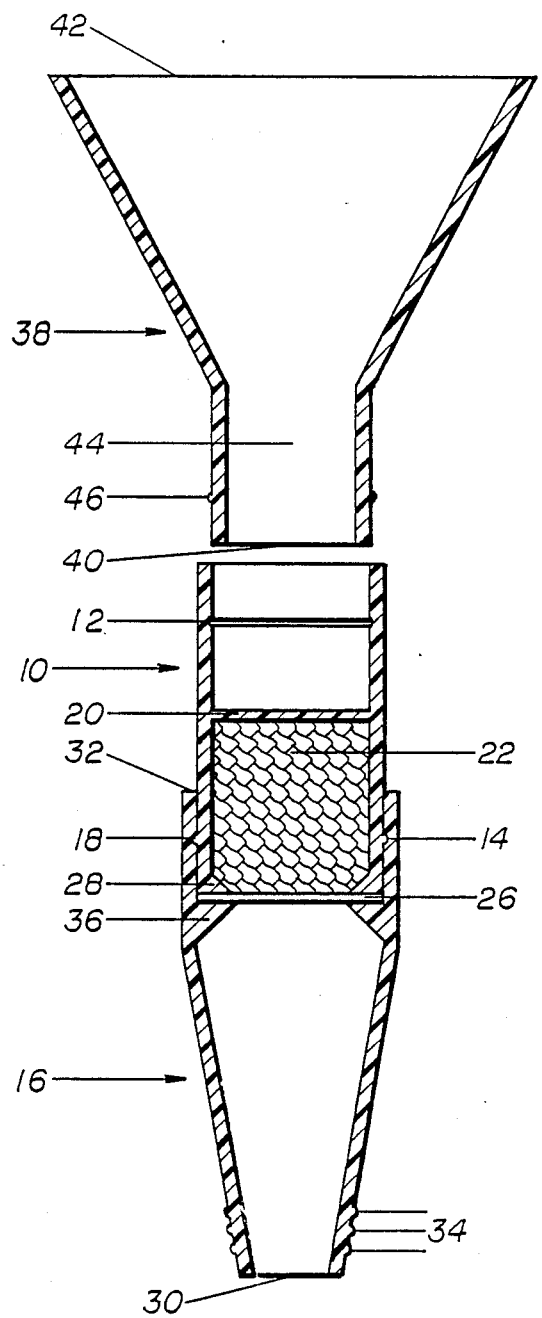
FIG. 9 is a cross-sectional side view showing the device of FIG. 7 with the scraping portion removed and the funnel in position to be fastened to the device.
Figure 10:
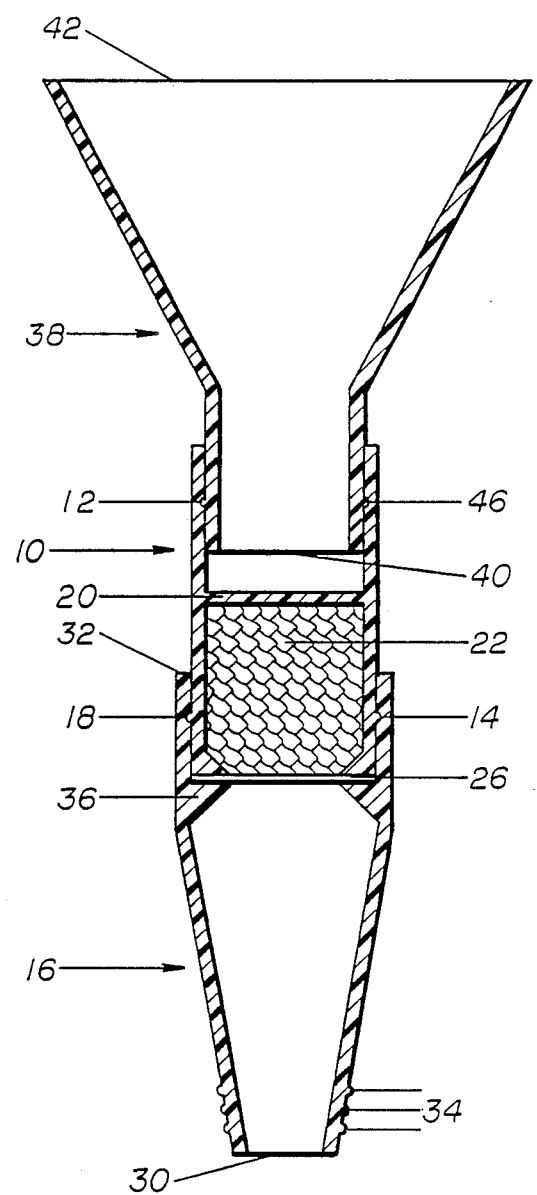
FIG. 10 is a cross-sectional view showing the device of FIG. 8 with the scraping portion removed and the funnel attached.

As shown in the embodiments of FIGS. 2 and 7, the device is composed of four primary parts. All parts with the exception of scraper 2 are radially symmetric.

Scraper 2 is shaped as a cone with its tip 4 sliced off at an angle aproximately 60 degrees from parallel to the base 6 of the cone. The length of scraper 2 is approximately three times the diameter of its base 6. Scraper 2 is hollow, the inside of the cone being smooth all the way from base 6 to sliced tip 4. The outside of scraper 2 is smooth from base 6 to apex 4 with the exception of a raised bead 8 around the circumference of the cone approximately $\frac{1}{3}$ of the distance from the base 6 to the tip 4. This bead 8 is approximately $\frac{1}{3}$ the chosen thickness for scraper 2 and will allow for an airtight "snap" together fitting with collector 10 by corresponding with a similar recess 12 around the inner surface of collector 10. With the exception of tip 4, scraper 2 is radially symmetric.

Collector 10 is cylindrically shaped. It is approximately twice as long as it is wide and about 4/5 the length of scraper 2. Collector 10 is hollow and its walls are approximately the same thickness as scraper 2. The inside diameter of collector 10 corresponds with the outside diameter of scraper 2. The outside of collector 10 is smooth along its entire length except for a raised bead 14 around the circumference of collector 10 about 4/5 of the distance along collector 10 from its end attached to scraper 2. Bead 14 is similar to raised bead 8 on scraper 2, being approximately $\frac{1}{3}$ the chosen thickness for collector 10. Bead 14 will allow for an airtight "snap" together fitting with vacuum attachment 16 by corresponding to a similar recess 18 around the inner surface of vacuum attachment 16. Across the width of collector 10 at approximately $\frac{1}{2}$ its length is a retaining screen 20. The size of the openings in screen 20 are not of great importance, needing only to be small enough to restrain primary filtering and retaining material 22 from moving out of reservoir 24 in the direction of scraper 2. Primary filtering and retaining material 22 is loosely packed in chamber 24 from retaining screen 20 to the end of collector 10 farthest from scraper 2. At this point primary filtering and retaining material 22 is bordered by a gas and liquid permeable filter 26. The inside of collector 10 is smooth along its entire length with the exceptions of recess 12, retaining screen 20 and a filter securing lip 28. Filter securing lip 28 gradually decreases the inside diameter of collector 10 at the end of collector 10 farthest from scraper 2. Filter securing lip 28 provides a greater area against which gas and liquid permeable filter 26 can be secured. Lip 28 begins approximately 1/5 of the length of collector 10 from vacuum attachment 16 and gradually increases the thickness of the walls of collector 10 in the direction of vacuum attachment 16 to approximately 2 ½ times their thickness elsewhere.

Vacuum attachment 16 is conically shaped similar to scraper 2 with its apex 30 sliced off not at an angle but parallel with its base 32. Vacuum attachment 16 is approximately 2 1/3 as long as its width. It is hollow, and the thickness of the walls of vacuum attachment 16 is similar to the thickness of the walls of scraper 2 and collector 10. The inside diameter of vacuum attachment 16 corresponds with the outside diameter of collector 10. The outside surface of vacuum attachment 16 is smooth from base 32 to apex 30 with the exceptions of a series of raised beads 34 around the circumference of vacuum attachment 16 to allow for a more secure and airtight attachment with a vacuum hose to which vacuum attachment 16 will be joined during operation. Series of raised beads 34 begin approximately 1/24 of the length of vacuum attachment 16 from the end of vacuum attachment farthest from collector 10, and continue for about ⅛ of the length of vacuum attachment 16 towards collector 10. Series of raised beads 34 are approximately ¼ to ⅓ the chosen thickness of vacuum attachment 16. The inside of vacuum attachment 16 is smooth from base 32 to apex 30 with the exceptions of recess 18, and filter holding lip 36. At a distance of approximately ¼ of the length of vacuum attachment 16 from base 32, filter holding lip 36 abruptly decreases the diameter and then gradually increases the diameter of the inside surface of vacuum attachment 16. The thickness of the walls of vacuum attachment 16 increase to approximately 3 ½ times their thickness elsewhere. The thickness gradually diminishes towards its original thickness approximately 4/13 of the length of vacuum attachment 16 from base 32.

Gas and liquid permeable filter 26 is disc shaped and the same diameter as the outside diameter of collector 10. Its thickness is not of great importance except that it needs to fit tightly and securely between filter securing lip 28 and filter holding lip 36, allowing air and liquid flow only through the filter 26 and not around the edges of the filter 26.

Funnel 38 is approximately three times as high as it is wide at base 40, and the same height as its width at top of funnel 42. The base of the funnel 40 has the same dimensions as the base of scraper 2 allowing for interchangeability with scraper 2 in attachment with collector 10. The width of the neck of the funnel 44 is constant for about ⅓ its height, where it flares out of the top of the funnel 42. The inside of funnel 38 is hollow and the surface is smooth from base 40 to top of funnel 42. Funnel 38 is of similar thickness as scraper 2, collector 10 and vacuum attachment 16. The outside surface of funnel 38 is smooth from base to apex with the exception of a raised bead 46 approximately 1/10 the the height of funnel 38 from base 40. Bead 46 has the same dimensions as raised bead 8, approximately ⅓ the chosen thickness of funnel 38 and allows for an airtight "snap" together fitting with collector 10 via the corresponding recess 12 on collector 10.

All four pieces, scraper 2, collector 20, vacuum attachment 16, and funnel 38 can all be manufactured in single pieces via injection molding. The retaining screen 20 can be molded in collector 10. The filter 26 can be specially manufactured, or the device can be manufactured to accomodate preexisting filters. Glass wool, cotton or other suitable primary filtration material is readily available.

While the above description contains many specifications, these are not to be construed as limitations on the scope of the invention, but rather as exemplifications of one prefered embodiment thereof. Other possible variations can be envisioned, but remain within the scope of my invention. A non-exhaustive treatment of the variations are listed below.

The connection 14 & 18 between collector 10 and vacuum attachment 16 can be one that will not allow disassembly once it is snapped together. This would be an attractive option if the device was marketed to be disposed of after use.

Collector 10 and vacuum attachment 16 can alternately be molded in one piece, inseparable at the position where the filter 26 is in the drawings. This amalgamation of collector 10 and vacuum attachment 16 may be molded with a slight indentation corresponding to the circumference of the disc filter 26 to ensure a tight fit between the filter 26 and the collector/vacuum attachment piece. After the primary filtering material 22 is inserted the retaining screen 20 can be wedged into the collector/vacuum attachment, or a recess corresponding to the circumference and position of the screen 20 can be molded into the collector/vacuum attachment as was done to accomodate the filter 26. The disadvantages are that the filter 26 is not easily exchanged and it will be difficult to ensure a tight fitting between the collector/vacuum attachment and the filter 26. This assembly does not afford the security of all parts as in the recommended means of manufacturing.

Alternately a porous plastic filter can be molded to correspond with the insided dimensions of the middle half of the collector/vacuum attachment (from about ¼ to ¾ of its length). This depth filter will perform the same function as the primary filtering material 22 and the disc filter 26, capturing the adsorbent in its pores and serving as a filter during elution. The porous plastic filter can be positioned by wedging it into the collector/vacuum attachment and employing a stiff retaining screen (with corresponding recessions molded in the collector/vacuum attachment to ensure tightness of fit) to secure it on the side of the filter near the base of the collector/vacuum attachment. The porous plastic filter could then be wedged into the collector/vacuum attachment, the protrusions preventing the filter from accidentially removing itself from the collector/vacuum attachment. This would alleviate the need for the retaining screen. Other means may be employed to secure the porous plastic filter. This method of construction is not recommended as porous plastic filters are more expensive and provide no low cost filter variation.

This invention is recommended to be made of polypropylene or other suitable moldable polymer, but it is not restricted to such material. If a glass apparatus is needed for compatibility with a given solvent, the funnel 38, collector 10 and vacuum attachment 16 or the collector/vacuum attachment can be manufactured of glass, and scraper 2 of any given material as it will not be exposed to the solvent during elution. If made of polypropylene, glass or other suitable polymer, this invention is durable enough to be washed and reused, even autoclaved if necessary.

This invention can be used with just the primary filtering material 22 or with just the secondary disc filter 26 in any of its embodiments. However, with only the secondary disc filter 26, collection will be jeopardized as there will be no material in which the adsorbent can embed itself, hence the potential for adsorbent loss is great. Solely using the primary filtering material affords a measure of filtration, adequate for some procedures, but allows no variation in filtration porosity.

The primary filtering material 22 may be of cotton, glass wool or any other suitable material. The retaining screen 20 is not necessary in any of the embodiments but recommended to ensure the retention of the primary filtering material 22.

The secondary gas and liquid permeable disc filter 26 can be made of any suitable material: glass microfibers, cotton, acrylic copolymers, etc. A backing can be added as a filtering surface in any of the embodiments if more strength is required than that provided by the secondary filter alone.

The overall size of the device can be varied, specifically to accomodate differing volumes of adsorbent being scraped. Collector 10 or the collector/vacuum attachment piece can also be deliberately sized to accomodate preexisting funnels which provide a good seal instead of specifically manufactured funnels.

The snap together fittings 8 & 12, 14 & 18, 12 & 46 in all the embodiments may be replaced with screw together or other suitable fittings.

The color of the scraper can be varied and a company name and logo can be imprinted on the device.

The shapes and embodiments of this invention are not restricted to these in the drawings and can be altered to accomodate different manufacturing and molding methods and different parts used.

This does not constitute an exhaustive treatment of the many and varied ways this invention can be constructed. Accordingly, the scope of this invention is determined not by the embodiments illustrated via drawings and text, but rather by the appended claims and their legal equivalent.

OPERATION OF THE INVENTION

Figure 5:
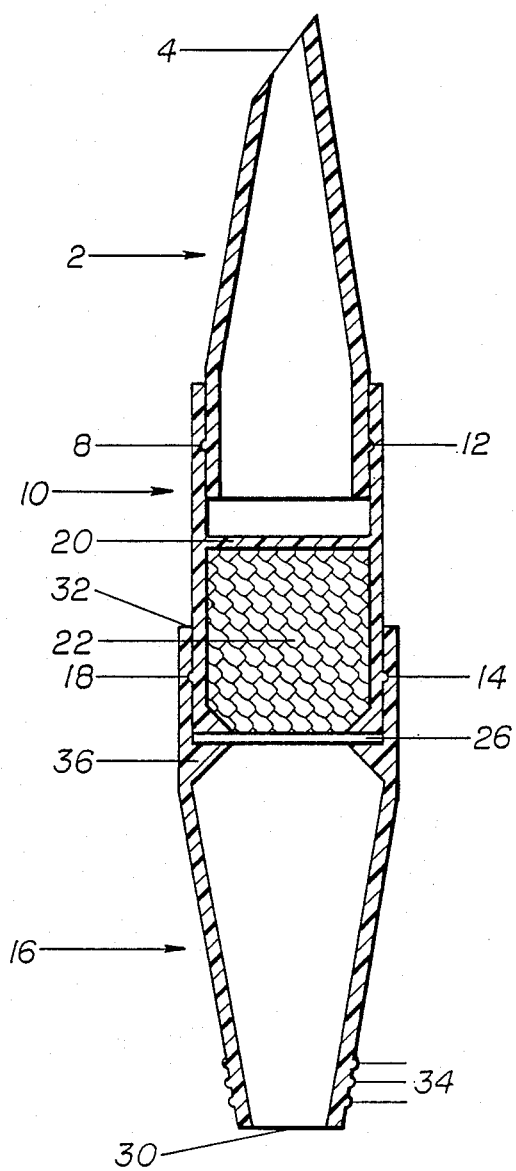
FIG. 5 is a cross-sectional side view showing the device of FIG. 1 assembled and ready for use.

In order to use this invention, it must be properly assembled as shown in FIGS. 1 and 5, and attached at the base of vacuum attachment 16 to a vacuum source via a flexible hose (not shown). After developing the thin layer chromatography plate and locating the areas to be collected, the slanted edge of scraper 2 is used to remove the adsorbent from the chromatography plate. The adsorbent will be aspirated up through scraper 2 into reservoir 24 where it is embedded in primary filtering material 22. The thin layer chromatography plate can easily be scraped clean with the contact the scraping edge 4 provides with the plate. Stray particles of adsorbent can be aspirated into the primary filtering material to ensure that no adsorbent is lost.

The user then gently and slowly separates scraper 2 from the rest of the device, keeping base 30 pointed towards the ground. Although the adsorbent is embedded in the primary filtering and retaining material 22, jerky movements should be avoided to ensure retention of all collected adsorbent. Attach funnel 38 to collector 10 in the same fashion that scraper 2 was connected. Hold the apparatus over a desired receptacle with the base 30 pointed into the receptacle. Aliquot a suitable solvent through the opening of the funnel 42. As the solvent passes through primary filtering material 22, it will draw the substance out of the absorbent and carry the substance and some of the adsorbent with it. As the eluate and the suspension of adsorbent arrives at the gas and liquid permeable filter 26, the adsorbent will remain in reservoir 24, but the solvent containing the substance will pass through the gas and liquid permeable filter 26 into the desired receptacle. Additional aliquots may be necessary to ensure complete elution of the substance. When the elution/filtration process is finished, the eluate can then be subjected to an evaporative technique; as the solvent evaporates, one is left with the pure recovered substance.

Filters 26 can be varied depending on the desired purity of the recovered substance, adsorbent particle size and the desired speed of filtration (larger porosity filters allow quicker filtration). To exchange filters 26, primary filtering material 22, or clean, the device can be separated into its component parts as shown in FIGS. 2 and 6. Primary filtering material 22 can be inserted into reservoir 24, and filter 26 can be placed against filter holding lip 32 inside vacuum attachment 16. With base 30 pointed toward the ground, the filter 26 will be held in place by the walls of vacuum attachment 16 as collector 10 is snapped together with vacuum attachment 16.

When handling many samples, a number of scrapers can be used simultaneously to save time. As each sample requires a different scraper, each can be separated into their respective parts and the elution process can be done on all the samples simultaneously. No time is lost while waiting for the solvent to pass through the primary filtering and retaining material and secondary filter.

If collection of the adsorbent is all that is required the primary filtering material can be removed to allow easy recovery of the adsorbent.

CONCLUSION AND SCOPE OF THE INVENTION

This device was invented to eliminate the time consuming, cumbersome and inaccurate means of manipulating developed samples on thin layer chromatography plates. The reader will see that this device provides the scientist with the following advantages: it facilitates the process, saves time and improves experimental reliability.

The invention will allow for the facile removal of the adsorbent from the plate, will ensure the retention of virtually all the adsorbent during collection, and will allow for the facile elution and purification of the sample. This is accomplished with normal use of laboratory equipment, minimizing time spent in preparation and cleanup to allow maximum use of time. All this can be accomplished at low cost to the scientist.

The use of this invention is not limited to thin layer chromatographic applications. Any time a substance needs to be removed collected and eluted to recover a soluble element contained in said substance, this invention can be considered for use.

I claim:

1. A device for the removal and collection of anhydrous particulate media, and for the extraction of substances from said media, comprising:
   (a) a rigid but flexing surface for manipulating said media;
   (b) a reservoir located inside said device of sufficient size to accomodate the volume of collected media;
   (c) a filtration means for retaining said media in said reservoir during extraction of said substance from said media; and
   (d) connection means for connecting said device to a vacuum source wherein said vacuum causes the removed media to pass into said reservoir, said device being separable into a plurality of parts.

2. The device of claim 1, wherein said filtration means includes a removable, exchangeable and therefore variable filter.

3. The device of claim 1, wherein (a) said rigid but flexing surface is located on a first piece which is attached to a second piece having said reservoir located therein;

(b) said connection means is located on a third piece which is attached to said second piece; and (c) said filtration means is located in said device in a fashion whereby all solids, liquids and gasses must pass through the filtration means to pass through the device.

4. The device of claim 1, wherein said reservoir for the collection of media is located posteriorly with respect to the direction of gas flow to a retaining screen, and anteriorly with respect to the direction of gas flow to a removable, exchangeable and therefore variable filter.

5. The device of claim 1, wherein said reservoir contains a material in which said media is easily embedded but removed only with significantly more effort than necessary to embed said media in said material.

6. The device of claim 1, wherein said device is constructed of such material to allow intentional and economical disposal after use.

7. The device of claim 1, wherein the components of said device are easily disassembled and reassembled with common hand strength and dexterity.

8. The device of claim 1, wherein the functions of removal, collection and extraction are accomplished within said device whereby;

(a) probability of loss of said media containing said substance is not increased due to transfer of said media; and (b) said functions are accomplished without additional laboratory apparatus.

9. The device of claim 1, further comprising a funnel addable to said device whereby a larger volume of solvent is added to a larger area whereby the said extraction of said substances from said media is facilitated.

10. A kit for removing anhydrous particulate media from a surface, for collecting said media, and for subjecting the collected media to elution and filtration whereby substances embedded in said media are recovered with greater ease, less time, cost and equipment than present methods comprising:

(a) a rigid but flexible edge for scraping and removing media attached to a surface;

(b) a collection and retention means adjacent to said rigid but flexible edge for collecting and retaining the volume of removed media;

(c) a filtration means for separating said media from said substances; and (d) an attachment means adjacent to said collection means whereby said kit is attached to a vacuum source.

11. The kit of claim 10, further comprising a funnel having a larger opening than the piece to which it attaches, addable or interchangeable with another piece in said kit whereby the addition of larger volumes of solvents are added to a greater area to facilitate the processes of elution and filtration.

12. The kit in claim 10, having a plurality of pieces, comprising:

(a) a first piece having said rigid but flexible edge for removing said media when adhered to a surface;

(b) a second piece connected with said first piece having said collection and retention means therein for collecting and retaining the removed media;

(c) a third piece connected to said second piece having said attachment means for connection to a vacuum source; and (d) a fourth piece interchangeable with said first piece for connection to said second piece, said fourth piece having a larger diameter opening than the diameter of said second piece.

13. The kit in claim 10, wherein said filtration means is removable and exchangeable, and therefore variable.

14. The kit in claim 10, wherein some pieces are constructed of polypropylene and intended to be disposed of after use.

15. A method using a single device for recovering substances from anhydrous particulate media, comprising the steps of:

(a) detaching said media from a surface with a rigid but flexible scraping edge on said device;

(b) aspirating the detached media from said surface via collection of said device to a vacuum source;

(c) collecting the aspirated media in a chamber located in said device;

(d) separating said device to provide a larger opening through which a liquid can be introduced into said device;

(e) aliquoting a solvent over said media remaining in said device, whereby said substances are eluted from said aspirated media; and (f) filtering the resultant eluate through a filtration means located in said device, whereby said anhydrous particulate media is separated from said eluate and retained in said device.

16. The method in claim 15, further comprising the steps of:

(a) collecting media free eluate in a receptacle;

(b) evaporating said solvent from said eluate to recover said substance in a dry pure form.

17. The method in claim 15, further comprising the attachment in a manner impermeable to solids, liquids and gasses of a funnel to the separated device to allow an even larger opening through which a liquid may be introduced into said device and to allow a greater volume of said liquid to be introduced during a given aliquot of said liquid.

18. The method in claim 15, further comprising having a means for retaining said media in said chamber irrespective of position of said device with respect to gravity or detachment of said device from said vacuum source.

19. The method in claim 15, further comprising the pre-intentional disposal of some (or all) of said device after use.

20. The method in claim 15, further comprising removing, exchanging and therefore varying said filtration means when differing porosity filtration is required.

* * * * *